US006495098B1

(12) United States Patent
Lea

(10) Patent No.: US 6,495,098 B1
(45) Date of Patent: Dec. 17, 2002

(54) METHOD AND APPARATUS FOR FLOWING STERILE ULTRA-THIN FLUID MEMBRANES

(75) Inventor: Peter Lea, Toronto (CA)

(73) Assignee: Biophys, Inc., Toronto (CA)

( * ) Notice: Subject to any disclaimer, the term of this patent is extended or adjusted under 35 U.S.C. 154(b) by 0 days.

(21) Appl. No.: 09/596,122

(22) Filed: Jun. 16, 2000

(30) Foreign Application Priority Data

Jun. 18, 1999 (CA) .............................................. 2275467

(51) Int. Cl.$^7$ .............................. A61L 2/08; A61L 2/10
(52) U.S. Cl. ......................... 422/24; 422/186.3; 422/28
(58) Field of Search ............................. 422/24, 28, 46, 422/186.3; 604/4; 250/436

(56) References Cited

U.S. PATENT DOCUMENTS

| | | | | |
|---|---|---|---|---|
| 4,228,125 A | * | 10/1980 | Lobdell et al. | 422/46 |
| 4,482,809 A | * | 11/1984 | Maarschalkerweerd | 250/436 |
| 5,133,932 A | | 7/1992 | Gunn et al. | 422/24 |
| 5,261,874 A | * | 11/1993 | Castle | 604/4 |
| 5,861,123 A | | 1/1999 | Schifftner | 422/24 |
| 5,871,459 A | * | 2/1999 | Muller | 604/4 |
| 5,882,591 A | * | 3/1999 | Kekez | 422/28 |

FOREIGN PATENT DOCUMENTS

| | | | |
|---|---|---|---|
| EP | 0 990 442 A1 | 5/2000 | A61K/31/40 |

OTHER PUBLICATIONS

PCT International Search Report–International application No. PCT/CA 00/01486 (Dec. 14, 2000).

* cited by examiner

*Primary Examiner*—Robert J. Warden, Sr.
*Assistant Examiner*—Sean E. Conley
(74) *Attorney, Agent, or Firm*—Dimock Stratton Clarizio LLP; Mark B. Eisen

(57) ABSTRACT

A method is provided for sterilizing fluids using bolus dosing of a fluid, stretching of the bolus of fluid into a membrane, such as a thin or ultra-thin film, and subsequent irradiation of the individual fluid membranes which are then recollected after sterilization. A system is provided whereby a fluid moves along a defined pathway in traditional bolus flow where each bolus of fluid is interspersed with a bolus of gas. The bolus of fluid, for example from a patient or other sample, moves along the flow path and the width of the flow path is gradually increased until the fluid bolus is stretched (without breaking) to form a thin fluid membrane which can be completely panned using irradiation (such as ultraviolet irradiation) to sterilize the each bolus which has been stretched into a membrane. After sterilization the width of the flow path is gradually narrowed to a sufficient sized such that the bolus returns to a sufficient size to be collected, typically when it forms a small droplet. The collected portions are recombined thereby rendering the original fluid sample completely sterilized for subsequent reintroduction into a patient or other use.

22 Claims, 1 Drawing Sheet

METHOD AND APPARATUS FOR FLOWING STERILE ULTRA-THIN FLUID MEMBRANES

FIELD OF THE INVENTION

This invention relates to a novel method for sterilizing fluids in a fluid sample including treatment of biological fluids for reintroduction into a human or other animal.

BACKGROUND OF THE INVENTION

Sterilization of fluids is important in many processes including certain medical treatments. Because fluids have a certain defined volume it is hard to ensure that the entire sample is sterilized and penetration of sterilizing agents remains an ongoing challenge in sterilization processes.

Irradiation is one method by which some have tried to sterilize fluids. The amount of penetration of the irradiation is proportional to the energy level of the irradiation and also to the particulate content in the sample. For example, higher energy levels of UV light will penetrate a sample further but the thickness of the sample remains a constraint on the success of this technique, even when the sample is poured into a thin layer on a surface. At best there is sterilization around the periphery of the sample and this may not be sufficient to address the needs of the end user. Stirring of the sample is often not an adequate solution to this problem.

The thickness of the fluid layer is controlled, amongst other things, by the viscosity of the fluid, the surface tension of the fluid and the speed of flow of the fluid if it is moving. Many current methods involve sterilization of fluids as they move since the fluid is often being treated before being restored back into the original sample or directly back into the person or animal. Even methods in which the fluid moves along a surface or in tubing still must overcome the penetration hurdle in order to optimally sterilize the fluid. The depth of penetration will depend on the film thickness but generally penetration depth will be less than ½ the film thickness. Particulates in the sample will decrease penetration depth even more.

There are presently many examples of sterilization methods for fluids, in particular biological fluids, which incorporate ultraviolet irradiation in the sterilization process. U.S. Pat. No. 5,709,991 of Lin, et al. teaches methods for photodecontamination to inactive microorganisms in platelet preparations involving the use of psoralens. The method also includes step(s) for the removal of the psoralens after photodecontamination. The need for removal of psoralens after decontamination remains a constraint on the suitability of this approach for certain biological fluids.

Others have tried to reduce the volume of the sample by spreading the fluid out on a surface or using mesh whereby the fluid is stretched in the mesh but these methods do not permit a continuous flow system. These and other methods have been tried to increase the surface area which is exposed to the sterilization agent. UV irradiation has fallen into lesser use because of problems achieving full penetration of the UV light though the whole sample. The advantage of UV light is that it acts to disable the nucleic acids in microorganisms such as viruses and bacteria. Similarly certain cells can be disabled or killed by UV irradiation. White blood cells and any other cells containing nucleic acids will also be effectively made sterile when irradiated. Red blood cells however do not contain a nucleus or nucleic acids and will therefore not be similarly affected.

SUMMARY OF THE INVENTION

In accordance with an aspect of the present invention a method is provided for converting a volume of fluid into a continuous flow of thin and ultra thin portions of the fluid referred to as "membranes" in this patent application. These membranes are so thin that irradiation, for example ultraviolet irradiation, will easily pan through the entire thickness of the membrane to effectively provide total sterilization in each fluid membrane portion. In accordance with another aspect, the method of the present invention can be used on clear fluids as well as fluids which contain particulates such as cells or other particles.

The principle of bolus flow using gas to create separate boli of fluid, or portions of a fluid sample, is coupled with a subsequent stretching of each fluid bolus into an extremely thin membrane which is then irradiated to achieve sterilization of that portion. The sterilized portions are later recombined and the complete fluid sample is effectively sterilized by this process.

The present invention has an advantage of providing a controlled system whereby fluid can be taken from one system, sterilized and then reintroduced into the original system after sterilization in a continuous flow system The thinness of the membranes advantageously allows for excellent and thorough sterilization of the fluid.

In accordance with an aspect of the present invention a method for sterilizing fluids is provided. The method comprises the steps of:

- bolus dosing the fluid into a fluid flow system using a gas to create a continuous path of bolus volumes of the fluid interspersed with the gas;
- moving the bolus volumes of fluid and gas in a continuous flow path through the system wherein the flow path gradually increases in width such that the fluid bolus is stretched into a fluid membrane, penetrable by irradiation;
- sterilizing each stretched fluid membrane by exposing it to a sufficient dose of irradiation;
- after sterilization, gradually narrowing the flow path width thereby increasing the thickness of each fluid membrane until it forms a droplet or is of suitable size to be collected; and
- collecting the sterilized fluid droplets.

In accordance with a preferred embodiment of the present invention the fluid membrane is stretched to form a thin or ultra-thin film.

In accordance with another aspect of the method of the present invention the irradiation is ultraviolet irradiation (UVI) and/or the fluid flow system is comprised of UV penetrable tubing wherein the diameter of the tubing is gradually increased and then later decreased in accordance with the claimed method steps. In one embodiment the tubing may be catheter tubing.

In accordance with another aspect of the present invention a further step of debubbling is introduced prior to collecting the fluid droplet to prevent frothing of the fluid. In another embodiment the fluid is recondensed before collection. In yet another embodiment the fluid is taken directly from a patient, treated and introduced directly back into the patient.

In accordance with another aspect of the present invention, there are multiple cycles of the method steps to permit repeat sterilizations before collection.

Fluid samples which are treatable by the present invention include any biofluid including whole blood, plasma, serum, and vaccine sera.

In accordance with another aspect of the present invention a method is provided for inactivating one or more microorganisms in the preparation of a vaccine, the method comprising the steps of:

bolus dosing the fluid into a fluid flow system using a gas to create a continuous path of bolus volumes of the fluid interspersed with the gas;

moving the bolus volumes of fluid and gas in a continuous path through the system wherein the flow path gradually increases in width such that the fluid bolus is stretched into a fluid membrane, penetrable by irradiation;

sterilizing each fluid membrane as it moves through the system by exposing it to a sufficient dose of irradiation to inactivate the one or more microorganisms;

after sterilization, gradually narrowing the width of the flow path thereby increasing the width of each fluid membrane/bolus until it forms a droplet or is of suitable size to be collected; and collecting the sterilized fluid droplet.

BRIEF DESCRIPTION OF THE DRAWINGS

For the purpose of illustrating the invention, there is shown in the drawings a form which is presently preferred. It is not intended that this invention be limited to the precise arrangements and instrumentalities shown. The present invention will be described in detail with reference to the accompanying drawings, in which like numerals denote like parts in the several views, and in which.

DETAILED DESCRIPTION OF THE PREFERRED EMBODIMENTS

Figure 1:
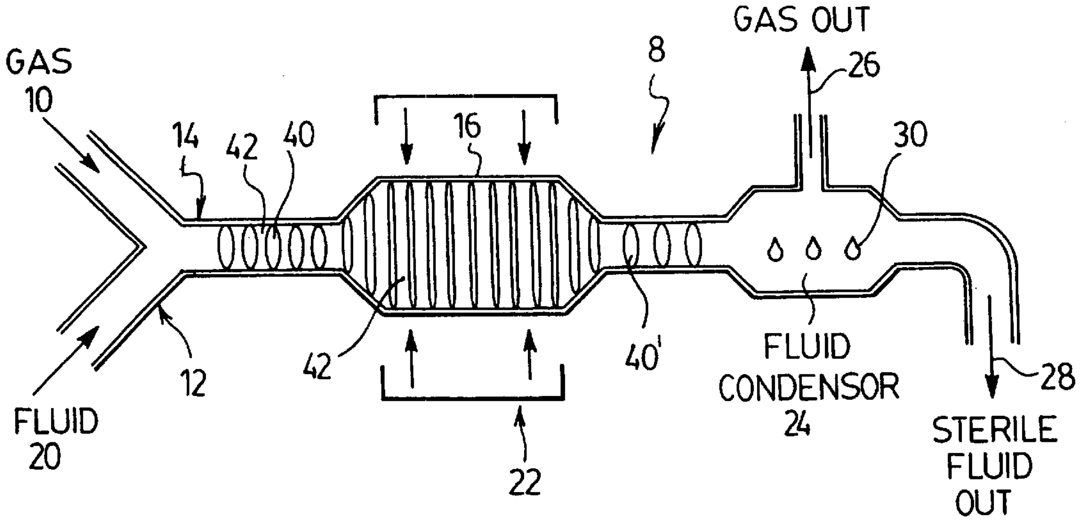
FIG. 1 is a schematic drawing of fluid membrane flow of a tubing substantially in cross section.

The present invention relates to a method of sterilizing fluids by incorporating the principle of bolus flow of a fluid together with the concept of irradiation. In accordance with the principle of the present invention fluid is moved along specially designed tubing in small bolus portions, as each bolus of fluid permits the greater penetration of the irradiation into the sample by stretching each bolus into a fluid membrane in a process defined herein as "fluid membrane flow" (FMF). After stretching, the fluid membrane has a thickness which approximates the thickness of the surface of a soap bubble.

The method of the present invention has applications for fluids and fluids which do not contain particulates (clear fluids) and fluids which do contain particulates (particulate fluids).

Bolus flow of fluids was first recognized in the 1950's as a method for movement of fluids in small volumes. This technique is schematically illustrated in FIG. 1 which shows that a gas (10) and a fluid (20) are individually and intermittently introduced into tubing (12). The fluid (20) flows interspersed by the gas (10) such that a series of boli (40) of fluid are interspersed by gas (42) in the tubing (14). The volume and the speed of flow of the fluid along the tubing (12) and the boli along tubing (14) are regulated by the flow of the gas and also by controlling the respective partial pressures of the fluid and the gas in the system. Therefor, in the present invention the tubing is modified, as illustrated by reference numeral 16 in FIG. 1, to expand the diameter. As the diameter of the tubing expands each fluid bolus is stretched as it portions through the wider diameter portion of the tubing.

In the fluid membrane flow (FMF) system of the present invention, the tubing is designed to have a portion which is wider in one section (16) and as the bolus (40) moves along first narrower portion (14) of the tubing (12) it is stretched as it passes along the wider portion (16) thereby decreasing the thickness of the fluid membrane while increasing the surface area of the fluid membrane. The width of the tubing in the wider portion (16) is selected such that the fluid membrane is stretched to have a thickness of several nanometers preferably <50 nanometers as measured by light diffraction colours. For example, a membrane thickness of 50 to 60 nm is grey in colour. The important fact is when the fluid membrane is stretched, the fluid portion of the fluid membrane is fully exposed to the irradiation and therefore can be completely sterilized.

At the wider portion of the tubing (16) the fluid membranes (42) are stretchable to ultrathin films and it is here that irradiation (22) is applied to the thin fluid membranes.

In one embodiment the tubing (14) connects to a fluid condenser (24) at which the fluid membrane/bolus condenses into droplets (30). The gas (10) can be removed through a port (26).

In one embodiment, the FMF system of the present invention comprises tubing which is penetrable by irradiation, and preferably by ultraviolet irradiation (UVI). One skilled in the art would know of other types of irradiation which would work. In a preferred embodiment, the fluid membrane is exposed to UVI from outside the tubing, the UVI penetrates the tubing and then penetrates the thin or ultra-thin fluid membrane (formed by stretching the fluid bolus) thereby sterilizing it and inactivating any microorganisms which may be present. The tubing itself is also sterilized by this preferred methodology. The UV irradiation may also inactivate nucleated cells, including lymphocytes and those cells containing virus particles of genomes, for example, by crosslinking the respective nucleic acids.

Advantages of using UVI for sterilization are that there is no washing step required and no contaminants are created. It is a useful process for dialysis patients and also for vaccine preparation since the UVI should not alter the antigenic structure of the organism but effectively prevents the organism from reproducing by damaging its nucleic acids(s).

Although the preferred embodiments described herein are described with respect to the testing of human biologic samples it is well understood that such assays and methodologies could equally be used for assessing biologic samples in other animals. In particular the present invention would clearly have applicability to veterinary services.

Those skilled in the art will recognize, or be able to ascertain using no more than routine experimentation, many equivalents to the embodiments of the invention described specifically above. Such equivalents are intended to be encompassed in the scope of the following claims.

I claim:

1. A method for sterilizing a fluid, comprising the steps of:

a. bolus dosing the fluid along a fluid flow path using a gas to create a continuous flow of bolus volumes of the fluid interspersed with the gas along the flow path;

b. moving the bolus volumes of fluid and gas along the flow path to a wider portion of the flow path, wherein the fluid bolus is stretched to form a fluid membrane having a thickness penetrable by a sterilizing dose of irradiation;

c. sterilizing each fluid membrane, as it moves along the wider portion of the flow path, by exposing each fluid membrane to irradiation sufficient to sterilize the fluid membrane; and d. collecting the sterilized fluid.

2. The method according to claim 1 wherein the width of the flow path gradually narrows downstream of the wider portion of the flow path, thereby causing the fluid membrane to increase in thickness for collection.

3. The method according to claim 2 wherein the flow path is tubing.

4. The method according to claim 3 wherein the tubing is a catheter.

5. The method according to claim 3 wherein the tubing is penetrable by irradiation.

6. The method according to claim 5 wherein the irradiation is ultraviolet irradiation.

7. The method according to claim 1 further comprising the additional step of debubbling the fluid after the sterilizing step to reduce frothing of the fluid.

8. The method according to claim 2 wherein the fluid is collected in a condenser.

9. The method according to claim 2 wherein the method steps are repeated through multiple cycles.

10. The method according to claim 1 wherein the fluid is selected from the biofluid group including whole blood, plasma, serum and vaccine sera.

11. The method according to claim 1 wherein the fluid comprises one or more micro-organisms.

12. The method according to claim 1 wherein the fluid membrane is stretched to form an ultra-thin film.

13. The method according to claim 1 used for deactivating a micro-organism in the preparation of a vaccine.

14. An apparatus for sterilizing a fluid, comprising a fluid flow path having a first narrower portion having a gas inlet and a fluid inlet, for creating a continuous flow of bolus volumes of the fluid interspersed with gas along the flow path, and a wider portion, wherein the fluid bolus is stretched to form a fluid membrane having a thickness penetrable by a sterilizing dose of irradiation, and a source of irradiation, whereby each fluid membrane moving along the wider portion of the flow path is exposed to irradiation sufficient to sterilize the fluid membrane.

15. The apparatus of claim 14 wherein the wider portion of the flow path gradually narrows downstream into a second narrower portion of the flow path, whereby the fluid membrane moving out of the wider portion gradually increases in thickness for collection.

16. The apparatus of claim 15 wherein the flow path is formed by tubing.

17. The apparatus of claim 16 wherein the tubing comprises a catheter.

18. The apparatus of claim 16 wherein the tubing is penetrable by irradiation.

19. The apparatus of claim 18 wherein the source of irradiation is a source of ultraviolet irradiation.

20. The apparatus of claim 15 wherein the fluid is collected in a condenser.

21. The apparatus of claim 14 wherein the fluid membrane is stretched to form an ultra-thin film.

22. The apparatus of claim 14 deactivating a micro-organism in the preparation of a vaccine.

* * * * *